United States Patent
Sullivan et al.

(10) Patent No.: US 10,342,565 B2
(45) Date of Patent: Jul. 9, 2019

(54) SURGICAL SYSTEM WITH EXPANDABLE SHIELD

(71) Applicant: HOLOGIC, INC., Marlborough, MA (US)

(72) Inventors: Roy H. Sullivan, Uxbridge, MA (US); Ronald D. Adams, Holliston, MA (US); Paul DiCesare, Easton, CT (US); Jeffrey Radziunas, Wallingford, CT (US); Danial Ferreira, Milford, CT (US)

(73) Assignee: HOLOGIC, INC., Marlborough, MA (US)

( * ) Notice: Subject to any disclaimer, the term of this patent is extended or adjusted under 35 U.S.C. 154(b) by 795 days.

(21) Appl. No.: 14/782,867

(22) PCT Filed: Apr. 22, 2014

(86) PCT No.: PCT/US2014/034899
§ 371 (c)(1),
(2) Date: Oct. 7, 2015

(87) PCT Pub. No.: WO2014/176206
PCT Pub. Date: Oct. 30, 2014

(65) Prior Publication Data
US 2016/0045214 A1    Feb. 18, 2016

Related U.S. Application Data

(60) Provisional application No. 61/815,360, filed on Apr. 24, 2013.

(51) Int. Cl.
*A61B 17/32*    (2006.01)
*A61B 17/00*    (2006.01)
(Continued)

(52) U.S. Cl.
CPC .......... *A61B 17/32002* (2013.01); *A61B 2017/00557* (2013.01); *A61B 2017/320024* (2013.01);
(Continued)

(58) Field of Classification Search
CPC .... A61B 17/32002; A61B 2090/08021; A61B 2017/320024
See application file for complete search history.

(56) References Cited

U.S. PATENT DOCUMENTS 5,100,424 A * 3/1992 Jang .................. A61B 8/12
600/439
5,520,634 A    5/1996 Fox et al.
(Continued)

FOREIGN PATENT DOCUMENTS

WO    WO 1999/011184    3/1999
WO    WO 20141176206 A2    10/2014

OTHER PUBLICATIONS

PCT International Search Report and Written Opinion dated Dec. 2, 2014, for PCT/US2014/034899, Applicant Hologic, Inc., International filing date Apr. 22, 2014 (13 pages).

*Primary Examiner* — Alexander J Orkin
(74) *Attorney, Agent, or Firm* — Vista IP Law Group LLP

(57) ABSTRACT

A tissue removal system includes a morcellator having a cannula comprising a proximal end portion, a distal end portion, a sidewall, and at least one lumen extending between the proximal end portion and the distal end portion. A cutting blade is disposed within a lumen of the cannula. Also included is a tissue shield that has an expandable frame element and a shield element attached to the expandable frame element, wherein the tissue shield serves to isolate non-target tissues from at least the cutting blade of the
(Continued)

system so that such tissues remain unaffected by a surgical procedure conducted with the system.

15 Claims, 4 Drawing Sheets

(51) Int. Cl.
  *A61B 19/00* (2006.01)
  *A61B 90/00* (2016.01)
(52) U.S. Cl.
  CPC ............. *A61B 2019/481* (2013.01); *A61B 2090/08021* (2016.02)

(56) References Cited

U.S. PATENT DOCUMENTS

| | | | |
|---|---|---|---|
| 5,569,284 A * | 10/1996 | Young | A61B 17/32002 604/22 |
| 5,693,011 A | 12/1997 | Onik | |
| 5,730,752 A | 3/1998 | Alden et al. | |
| 5,906,615 A | 5/1999 | Thompson | |
| 6,004,330 A * | 12/1999 | Middleman | A61B 10/02 606/127 |
| 6,032,673 A | 3/2000 | Savage et al. | |
| 6,039,748 A | 3/2000 | Savage et al. | |
| 6,051,008 A * | 4/2000 | Saadat | A61B 17/3207 606/15 |
| 6,558,349 B1 * | 5/2003 | Kirkman | A61M 25/0082 604/104 |
| 6,673,090 B2 * | 1/2004 | Root | A61B 18/1492 606/200 |
| 7,226,459 B2 | 6/2007 | Cesarini et al. | |
| 2004/0167511 A1 * | 8/2004 | Buehlmann | A61B 18/1492 606/45 |
| 2006/0047185 A1 | 3/2006 | Shener et al. | |
| 2006/0206178 A1 * | 9/2006 | Kim | A61B 17/00234 607/96 |
| 2007/0005093 A1 * | 1/2007 | Cox | A61B 17/320016 606/198 |
| 2007/0213584 A1 * | 9/2007 | Kim | A61B 1/00082 600/104 |
| 2007/0213734 A1 * | 9/2007 | Bleich | A61B 17/00234 606/79 |
| 2008/0033467 A1 * | 2/2008 | Miyamoto | A61B 17/22 606/180 |
| 2008/0249553 A1 * | 10/2008 | Gruber | A61B 17/32002 606/171 |
| 2009/0062871 A1 * | 3/2009 | Chin | A61B 1/00082 606/86 R |
| 2009/0204119 A1 | 8/2009 | Bleich et al. | |
| 2009/0270812 A1 | 10/2009 | Litscher et al. | |
| 2009/0270898 A1 | 10/2009 | Chin et al. | |
| 2011/0196399 A1 * | 8/2011 | Robertson | A61B 17/22004 606/169 |
| 2012/0172889 A1 | 7/2012 | Chin et al. | |
| 2013/0053851 A1 | 2/2013 | Schmitz et al. | |

* cited by examiner

SURGICAL SYSTEM WITH EXPANDABLE SHIELD

RELATED APPLICATION DATA

The present application is a National Phase entry under 35 U.S.C § 371 of International Patent Application No. PCT/US2014/034899, having an international filing date of Apr. 22, 2014, which claims the benefit under 35 U.S.C. § 119 to U.S. Provisional Application Ser. No. 61/815,360, filed Apr. 24, 2013. The foregoing applications are hereby incorporated by reference into the present application in their entirety.

FIELD OF INVENTION

The disclosed inventions relate to surgical systems that include shield elements to protect tissue from unwanted contact during a surgical procedure.

BACKGROUND

There are many situations in which it is desirable to remove unwanted tissue from a patient. Uterine fibroids and uterine polyps are two examples of such unwanted tissue. Uterine fibroids are well-defined, non-cancerous tumors that are commonly found in the smooth muscle layer of the uterus. Uterine polyps are masses that are commonly found extending from the inner lining of the uterus. In many instances, uterine fibroids and uterine polyps can grow to be several centimeters in diameter and may cause, for example, menorrhagia (prolonged or heavy menstrual bleeding), pelvic pressure or pain, and reproductive dysfunction. It is believed that uterine fibroids occur in a substantial percentage of the female population, perhaps in 20 to 40 percent of all women, and that uterine polyps occur in up to 10 percent of all women.

One type of treatment for uterine fibroids and uterine polyps is hysteroscopic resection. Hysteroscopic resection typically involves inserting a hysteroscope into the uterus through the vagina, i.e., transcervically, and then cutting away the unwanted tissue from the uterus using a device delivered to the unwanted tissue by the hysteroscope. Hysteroscopic resections typically fall into one of two varieties. In one variety, an electrocautery device in the form of a loop-shaped cutting wire is fixedly mounted on the distal end of the hysteroscope—the combination of the hysteroscope and the electrocautery device typically referred to as a resectoscope. The transmission of electrical current to the uterus with a resectoscope is typically monopolar, and the circuit is completed by a conductive path to the power unit for the device through a conductive pad applied to the patient's skin. In this manner, tissue is removed by contacting the loop with the part of the uterus wall of interest. Examples of such devices are disclosed, for example, in U.S. Pat. No. 5,906,615, which is incorporated herein by reference.

In another variety of hysteroscopic resection, an electromechanical cutter is inserted through a working channel in the hysteroscope. The electromechanical cutter, sometimes referred to as a morcellator, is a motor-driven instrument that typically includes (i) a tubular member having an end or window through which tissue may enter and (ii) a cutting instrument positioned within the tubular member for cutting the tissue that has entered the tubular member. Suction or surgical grasping instruments are employed to draw tissue into the tubular member, which includes a cutting instrument that is used to cut the tissue into smaller pieces or "morcels." Examples of the electromechanical cutter variety of hysteroscopic resection are disclosed in, for example, U.S. Pat. Nos. 7,226,459; 6,032,673; 5,730,752; U.S. Publication No. 2012/0172889 A1; U.S. Publication No. US 2009/0270898 A1; U.S. Publication No. 2009/0270812 A1; U.S. Publication No. US 2006/0047185 A1; and PCT International Publication No. WO 99/11184; each of which is incorporated herein by reference. In other procedures to treat uterine fibroids and uterine polyps, laparoscopic morcellators are employed in a laparoscopic (rather than hysteroscopic) procedure. Examples of laparoscopic morcellators are described in U.S. Pat. Nos. 5,520,634 and 6,039,748, each of which is incorporated herein by reference.

It is generally desired to minimize the duration of surgical procedures such as hysterectomies. The tissue removal rates achievable with known morcellators and resection devices may be limited, thus resulting in surgical procedure durations that are longer than desired. Such devices may also be characterized by exposed cutting blades or surfaces, thus risking unintended tissue removal or damage. There is a need for surgical resection devices that provide a high rate of tissue removal while also protecting tissues that are not intended to be removed during a surgical procedure.

SUMMARY OF THE INVENTION

The disclosed inventions are directed to tissue removal systems and methods that may be used, without limitation, for removing uterine fibroids or other gynecological tissues. The tissue removal (i.e., surgical) systems and methods include means for protecting tissue that is intended to be unaffected during a surgical procedure.

In one embodiment, the tissue removal system includes a cannula comprising a proximal end portion, a distal end portion, a sidewall, at least one lumen extending between the proximal end portion and the distal end portion, and a cutting blade disposed within a lumen of the cannula. Also included is a tissue shield that includes an expandable frame element and a shield element attached to the expandable frame element. The tissue shield serves to protect non-target tissues from at least the cutting blade of the system so that such tissues are not contacted with the cutting blade during a surgical procedure conducted with the system.

The disclosed inventions further include a method of using a surgical tissue removal system in a resection procedure of target tissues. The system includes a cannula comprising a proximal end portion, a distal end portion, a sidewall, at least one lumen extending between the proximal end portion and the distal end portion, and a cutting blade within a lumen of the cannula. Also included is a tissue shield slideably coupled to the cannula, the shield, the tissue shield including an expandable frame element and a shield element attached to the expandable frame element. In one embodiment, a method according to the disclosed inventions includes the acts of expanding the expandable frame element to isolate non-target tissues from at least the cutting blade of the system with the shield element, and contacting target tissues with the cutting blade, while the expandable frame element is in an expanded configuration.

Additional aspects, features and advantages of the disclosed inventions are set forth in part in the description which follows, and will also in part be apparent from the description or may be learned by practice of the invention. In the description, reference is made to the accompanying drawings which form a part thereof and in which is shown by way of illustration various embodiments for practicing the disclosed inventions. Although the embodiments are described in sufficient detail to enable those skilled in the art to practice the disclosed inventions, it is to be understood that other embodiments may be utilized and that structural changes can be made without departing from the scope of the inventions as defined by the claims appended hereto. The following detailed description is, therefore, for purposes of illustration, and is not to be taken in a limiting sense.

DETAILED DESCRIPTION

Figure 1:
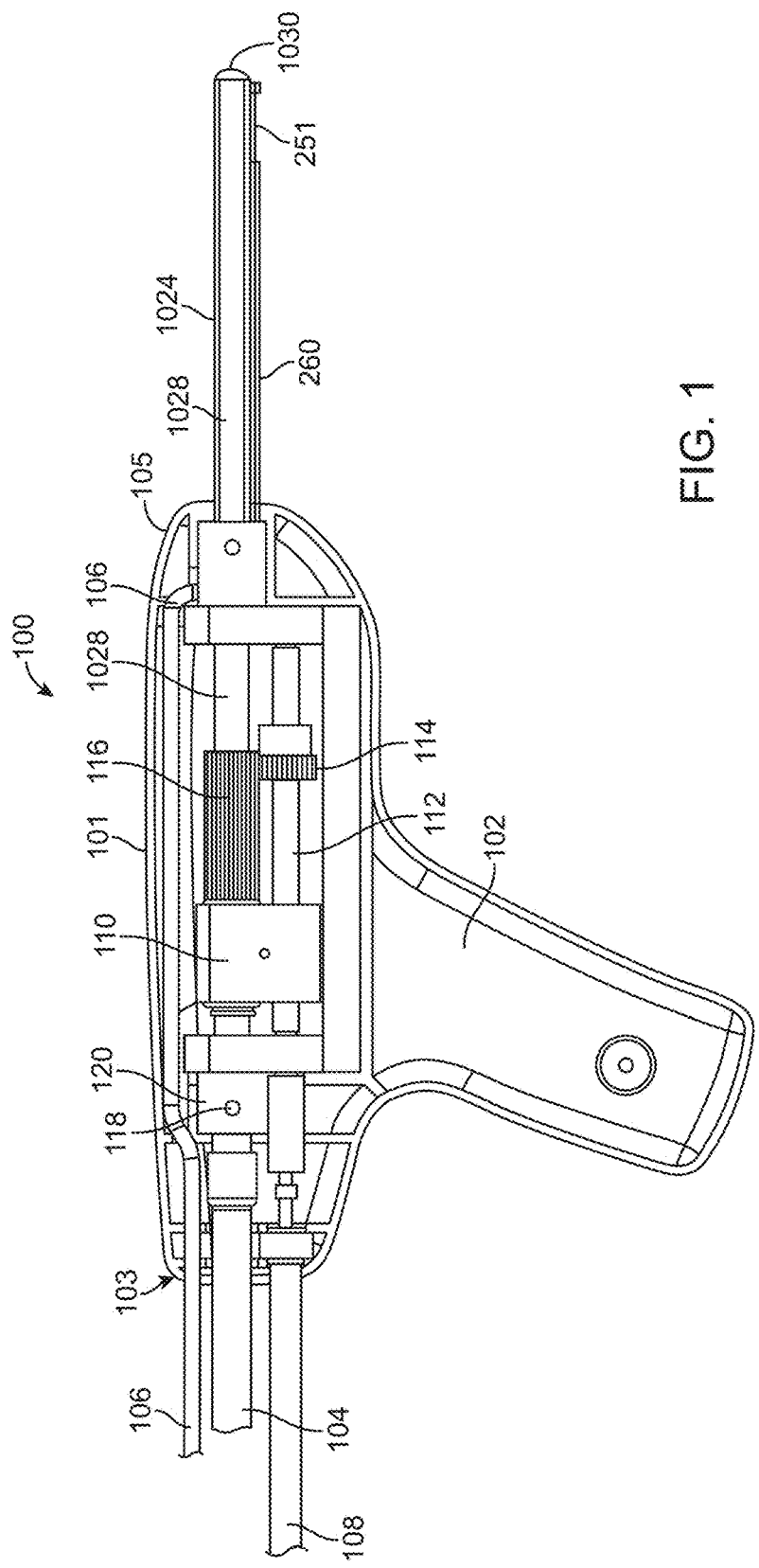
FIG. 1 is a cross-sectional view of an exemplary surgical access and tissue removal system for use with the disclosed inventions.

FIG. 1 schematically illustrates an exemplary surgical access and tissue removal system 100 for use with the current invention. As used herein, tissue "removal" is synonymous with tissue "resection" and generally refers to the surgical removal of tissue from a patient's body. A laparoscopic morcellator is used to illustrate the principles of the embodiments of the disclosed inventions. However, it will be understood that such principles apply equally to all types of surgical access devices, as well as to devices not necessarily limited to surgical access. Thus, the embodiments described with respect to a morcellator intended for gynecological procedures are illustrative only, and not intended to be limiting in any respect.

With further reference to FIG. 1, the exemplary laparosopic surgical access and tissue removal device 100 (i.e., a laparoscopic morcellator) may be considered a surgical access device 100 configured for gynecological procedures, such as a hysterectomy. In addition to the performance of one or more gynecological procedures described in detail herein, the systems, methods, apparatuses, and devices disclosed herein may be used to perform one or more additional procedures (for example, urological procedures or the like), including, but not limited to, access and tissue manipulation and/or tissue removal from any of a variety of organs and tissues, such as the bladder, breast, lung, stomach, bowel, esophagus, oral cavity, rectum, nasal sinus, Eustachian tubes, heart, gall bladder, spine, shoulder, knee, hip, brain, arteries, veins, and various ducts. Routes of access include but are not limited to trans-cervical; trans-vaginal-wall; trans-uteral; trans-vesicle; trans-urethral; trans-nasal; and other routes.

The exemplary surgical access and tissue removal device 100 illustrated in FIG. 1 is configured for removing tissue from the body, in this case fibroids and other abnormal tissue from the uterine cavity, or alternatively the uterus in its entirety. Tissue remove device 100 includes a housing 101 shown in cross-section. The housing 101 may comprise complementary left and right housing halves, each of which may be made of a rigid polymer or other suitable material, which are joined together, for example, with screws, adhesive, or other suitable means. The housing includes a handle 102 of any suitable size and shape to facilitate ease of use. Extending from the proximal end 103 of the housing 101 is a suction tube 104, and optional fluid line 106 and motor driver line 108. Extending from the distal end 105 of housing 101 is an outer tubular member 1024 having a lumen therein, which preferably terminates in a distal end 1030. Within the lumen of the outer tubular member 1024 is an inner tubular member 1028, as further described herein. In certain embodiments, a second lumen 260 extends at least partially along the outer tubular member 1024.

The suction tube 104 is preferably a flexible tube extending from a pump (not shown) or other vacuum source to the inner tubular member 1028. The suction tube 104 is in working fluid communication with the inner tubular member 1028 so that materials including solids, fluids and/or gases may be pulled through the inner tubular member 1028 and into the suction tube 104. In this manner, the vacuum source may be used to apply suction to the tissue removal device 100, and any withdrawn tissue, fluids, or other matter suctioned through the resection window 1026 of the tissue removal device 100 may be collected outside of the patient's body.

Figure 8:
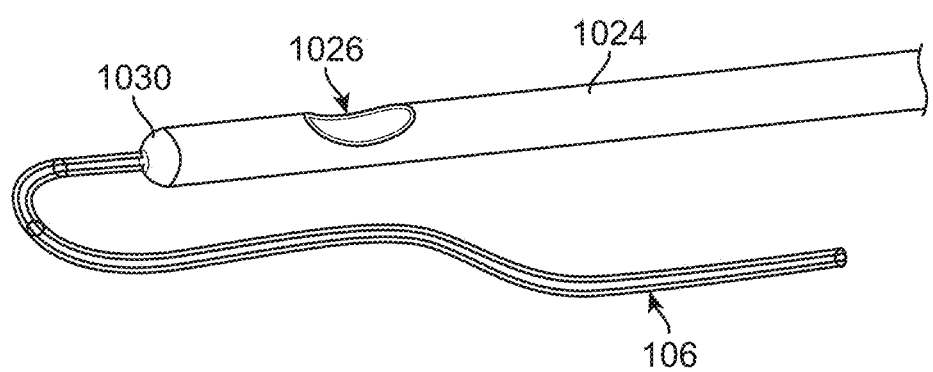
FIG. 8 shows an embodiment of the disclosed inventions in which a fluid line extends beyond the distal end of the outer tubular member of the devices of the disclosed inventions.

The fluid line 106 extends from a fluid source (not shown) into the housing 101. The purpose of the fluid line 106 is to deliver fluid, such as saline, to a surgical site. For example, the fluid may be delivered from the fluid line 106 into the space between the inner tubular member 1028 and the outer tubular member 1024, whereupon it flows towards the distal end 1030 of the outer tubular member 1024 and exits from the device 100 at the resection window 1026 described below. Alternatively, the fluid line 106 may continue as a separate lumen that extends within, or on the outside of, the tubular member 1024 and terminates at or near distal end 1030 of the outer tubular member 1024. Alternatively, the fluid line 106 extends through the outer tubular member and exits from (and extends beyond) the distal end 1030 of the outer tubular member 1024, as shown in FIG. 8. Alternatively, fluid is preferably delivered to a surgical site using methods and systems of the disclosed inventions with any suitable fluid delivery mechanism.

Figure 3:
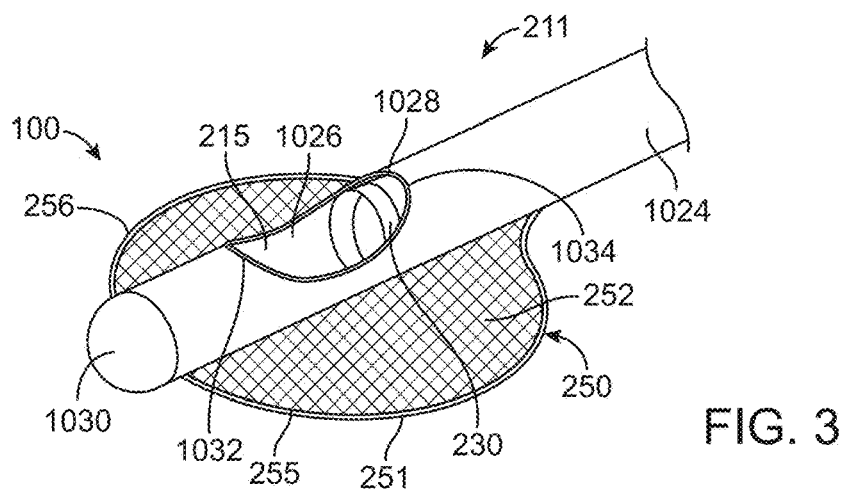
FIG. 3 is a perspective view of the distal end portion of a tissue removal device, in accordance with an embodiment of the disclosed inventions.

The optional delivery of fluid to a surgical site using the devices and systems of the disclosed inventions can result in many advantages. For example, some surgical procedures that make use of the systems and devices of the disclosed inventions are conducted within an insufflated cavity, such as a uterus. At the same time, such surgical procedures are conducted using suction to pull tissue through the resection window 1026 in the outer tubular member 1024, as shown in FIG. 3. The delivery of fluid to the surgical site creates a fluid environment in at least the area immediately surrounding the distal end 1030 of the outer tubular member 1024, thus creating a seal around the cut tissue that helps to facilitate such tissue withdrawal. Moreover, fluid delivery results in the lubrication of morcellated tissue, thus easing the movement of such tissue within the inner tubular member 1028.

In certain embodiments, the motor driver line 108 comprises an electrically conductive wire extending from a power supply (not shown) to a motor 110. Upon application of electrical current from the power supply, the motor 110 drives shaft 112 to rotate at a high rate of speed. Mounted on the drive shaft 112 is a first drive gear 114 having teeth that mesh with the teeth of second drive gear 116, which is mounted on the inner tubular member 1028. This configuration results in the rotation of the inner tubular member 1028 within the outer tubular member 1024. In certain embodiments, the second drive gear 116 extends along a length of the inner tubular member 1028 so that the inner tubular member 1028 may be moved in translation (i.e., parallel to a long axis thereof) while remaining engaged with the first drive gear 114. Such translational movement may be imparted manually by a pin 118 or other suitable structure extending within a longitudinal slot from the side of housing 101 and attached to a positioning component 120, within which the inner tubular member 1028 may freely rotate. Alternatively, translational movement may be imparted from the motor 110 using means known in the art. Alternatively, the inner tubular member 1028 rotates but does not otherwise move relative to the outer tubular member 1024. In the latter embodiment, target tissue may be brought into contact with an exposed, rotating blade.

Figure 2:
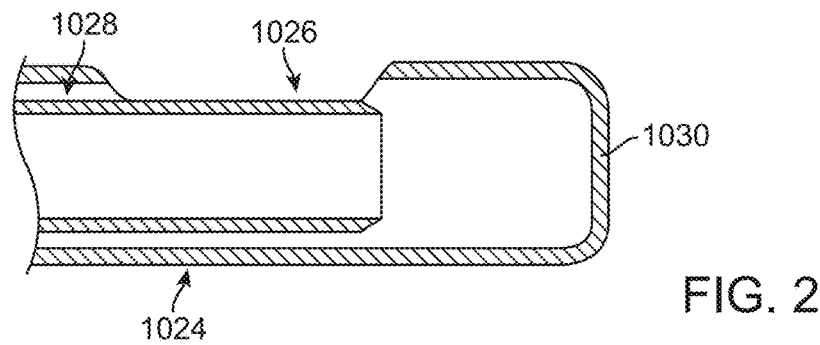
FIG. 2 is a cross-sectional view of the distal end portion of a tissue removal device, in accordance with an embodiment of the disclosed inventions.

FIG. 2 is a cross-sectional view of the distal end portion of the exemplary tissue removal device 100. Device 100 comprises an electromechanical cutting mechanism comprising an outer tubular member 1024 and an inner tubular member 1028, which may move rotationally and oscillate translationally relative to outer tubular member 1024. As shown, outer tubular member 1024 includes a resection window 1026.

When vacuum is applied to the inner tubular member 1028, the resection window 1026 may receive, capture, and/or draw in tissue, fluid, and/or other matter. The window 1026 may be located proximate to the distal end 1030, such as, for example, 0.25 inch from the distal end 1030. The window 1026 may be shaped to include a proximal end 1034 and a distal end 1032. The proximal end 1034 may slope gradually proximally, and the distal end 1032 may slope gradually distally. The proximal end 1034 of the resection window 1026 may be a radial end having a radius of curvature of, for example, 0.085 inches; however, other radius curvatures are possible. The distal end 1032 of resection window 1026 may be a radial end having a radius of curvature of, for example, 0.150 inches; however, other radius curvatures are possible. The slopes of the proximal and distal ends 1034, 1032 may allow or encourage tissue to enter the resection window 1026. In some embodiments, the slopes of the proximal and distal ends 1034, 1032 form cutting edges for tissue resection. The resection window 1026 may have a length of approximately 0.55 inches. However, other lengths are possible. The resection window 1026 may extend over a substantial portion of the circumference of the outer tubular member 1024, such as, for example, about 60% of the circumference; however, other percentages are possible.

The inner tubular member 1028 may include a proximal end, a distal end, and a longitudinal lumen. The distal end of the inner tubular member 1028 may be shaped to include an external bevel, such as, for example, an external bevel of approximately 20 degrees. Tubular members 1024 and 1028 may be arranged so that, when tubular member 1028 is in a fully retracted, proximal-most position, distal end of tubular member 1028 may be withdrawn sufficiently to permit tissue to enter window 1026 (such as with distal end of tubular member 1028 positioned proximal to window 1026), and so that, when tubular member 1028 is in a fully advanced, distal-most position, distal end of tubular member 1028 may be positioned distally of distal end 1032 of window 1026. In this manner, as tubular member 1028 is moved translationally and rotationally past window 1026, tissue within window 1026 may be sheared. To promote such a shearing of tissue, the outer diameter of inner tubular member 1028 may be just slightly less (e.g., about 0.002 inch) than the inner diameter of outer tubular member 1024.

Figure 4:
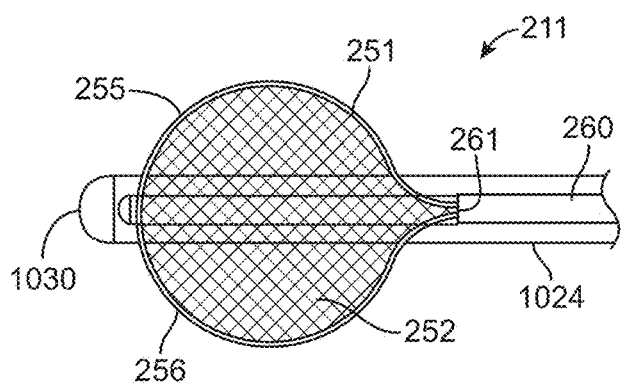
FIG. 4 is a bottom view of the distal end portion of a tissue removal device with a tissue shield in an expanded configuration, in accordance with an embodiment of the disclosed inventions.
Figure 5:
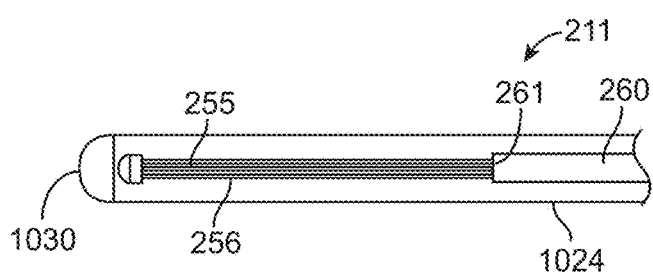
FIG. 5 is a bottom view of the distal end portion of a tissue removal device with a tissue shield in a retracted configuration, in accordance with an embodiment of the disclosed inventions.

All embodiments preferably include means for protecting non-target tissue, i.e., tissue that is intended to be unaffected by the surgical procedures described herein. For example, FIGS. 3-5 show a distal end portion 211 comprising the outer tubular member 1024 with the distal end portion 211 terminating in a closed distal end 1030. The outer tubular member 1024 has a lumen 215 extending therein between the distal end portion 211 and its proximal end 104 (shown in FIG. 1). The resection window 1026 is located in the sidewall of the outer tubular member 1024 within the distal end portion 211. The resection window 1026 exposes the lumen 215 to tissue located outside of the outer tubular member 1024, as previously discussed.

The tissue removal device 100 includes a cutting mechanism that includes a cutting blade 230 with a sharp edge, as is known in the art. The cutting blade 230 may be formed at the distal end of the inner tubular member 1028, as shown in FIG. 3, or may otherwise be an annular ring or other suitable configuration. The cutting blade 230 is slidably disposed within the lumen 215 such that it can move substantially between the proximal and distal ends 1034, 1032 of the resection window 1026. In addition, the cutting blade 230 may rotate as it moves laterally.

The embodiment shown in FIGS. 3-5 includes a tissue shield 250, which comprises an expandable frame element 251 and a shield element 252 attached to the expandable frame element 251. The tissue shield 250 may be placed in a retracted configuration (as shown in FIG. 5) for delivery into a patient, and an expanded configuration (as shown in FIGS. 4 and 5) for use during resection. FIGS. 4 and 5 are bottom views of the tissue removal device 100, and FIG. 3 is a perspective top view.

The expandable frame element 251 may be made from a shape memory material such as nitinol or a shape memory polymer that expands to the expanded configuration when released from forces that hold it in the retracted configuration. Alternatively, the expandable frame element 251 is inflatable such that pressurized gas or fluid may be delivered through an inflation tube or the like to cause the expandable frame element 251 to assume its expanded configuration. The frame element 251 may be of unitary construction, or may comprise multiple parts. For example, the first and second portions or "legs" 255, 256 of the frame element 251 may be portions of a single loop structure, or they may be separate pieces that are positioned together to form the frame element 251.

The expandable frame element 251 is generally circular in shape, although it may be any suitable shape, such as triangular, square, rectangular, and so forth. In the embodiment shown in FIGS. 3-5, the frame element 251 extends from a second opening 261 of a second lumen 260 that extends along the outer tubular member 1024 to the distal end portion 211. The second opening 261 is proximal to the resection window 1026 along the length of outer tubular member 1024. In the event that the frame element 251 is made from a shape memory material, in one embodiment a pull wire or similar element extends within the second lumen 260 and is attached to the frame element 251 so that it may be manipulated by a user located at the proximal end portion of the system to selectively apply forces to the frame element so that it may be manipulated between its expanded and retracted configurations. In the event that the frame element 251 is inflatable, a pressurized gas or fluid may be delivered to the frame element 251 via second lumen 260 or an inflation tube extending within second lumen 260 so that the frame element 251 may be manipulated between its expanded and retracted configurations.

A shield element 252 is attached to the expandable frame element 251 by any suitable mechanism. For example, the shield element 252 may be adhered to the frame element 251 with the use of an adhesive or via mechanical attachment such as by sutures. Alternatively, the shield element 252 may be formed with an annular sleeve or similar opening around its circumference such that the frame element 251 is placed therein, or the shield element 252 may be formed as an expandable cover that is placed over the frame element 251.

The shield element 252 is made from any suitable material. For example, in one embodiment the shield element 252 is an elastomeric polymer that stretches with the frame element 251 as it expands from its retracted configuration of FIG. 5 to its expanded configuration of FIGS. 3 and 4. In another embodiment, the shield element 252 is a metallic mesh. In either event, the tissue shield can be resilient such that it assumes a reduced configuration when the frame element 251 is in a retracted configuration and expands with the frame element 251 when the frame element 251 is expanded. When the frame element 251 is in a fully expanded configuration, the shield element 252 can be substantially taut, meaning that the shield element 252 provides a surface with sufficient mechanical integrity so that it can effectively protect the tissue that it is placed against the bottom side of the shield element during a surgical procedure (such as the bowel) by preventing the non-target tissue from contacting the cutting blade 230 or other cutting surface. As such, non-target tissue held against the shield element 252 will be prevented from entering the window 1026 whereas tissue proximate the window 1026 may freely enter the window 1026 for the resection thereof.

For embodiments of the disclosed inventions that include first and second openings (such as openings 1026 and 261 in the embodiment shown in FIGS. 3-5), they may be spaced about 180 degrees apart from each other, as shown in FIGS. 3-5. In other embodiments, openings are spaced at various other angles with respect to each other, such as at 15, 30, 45, 60, 75, 90, 105, 120, 135, 150, or 165 degrees from each other.

Figure 6:
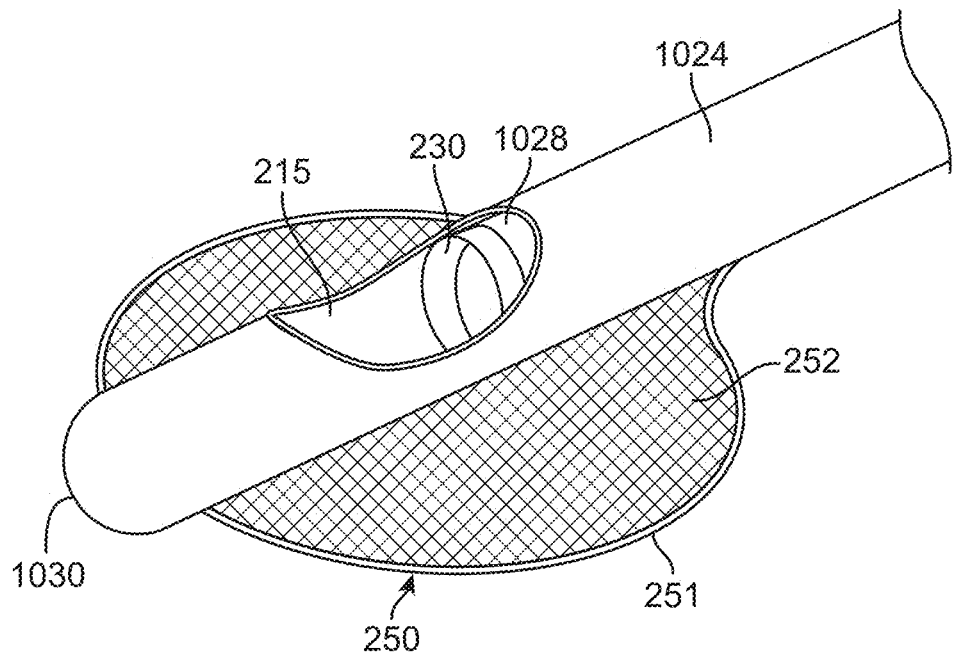
FIG. 6 is a perspective view of the distal end portion of a tissue removal device, in accordance with an embodiment of the disclosed inventions.
Figure 7:
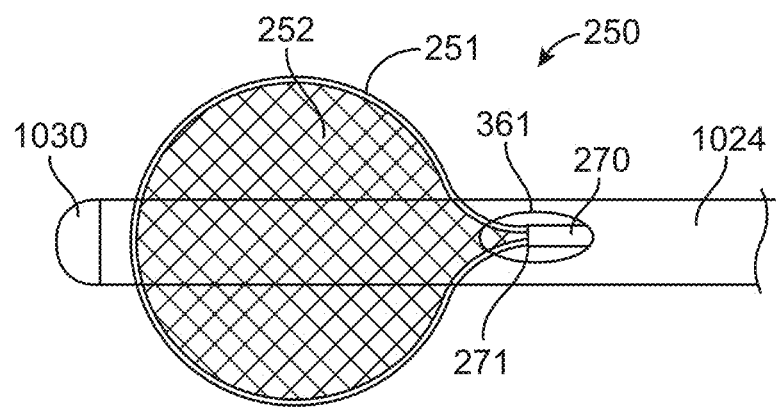
FIG. 7 is a bottom view of the distal end portion of a tissue removal device, in accordance with an embodiment of the disclosed inventions.

Although the embodiment shown in FIGS. 3-5 includes a second lumen 260 that extends at least partially along the underside of outer tubular member 1024 (see FIGS. 4 and 5), other embodiments do not include more than a single lumen, and still other embodiments include multiple lumens that are separated or at least partially connected, in either case entirely within a single cannula. For example, like the embodiment shown in FIGS. 3-5, the embodiment shown in FIGS. 6 and 7 includes a cutting mechanism that includes cutting blade 230 at the distal end of a tubular element 1028, where the cutting mechanism is located within the lumen 215 of the outer tubular member 1024. Unlike the embodiment of FIGS. 3-5, however, the tissue shield 250 of the embodiment of FIGS. 6 and 7 is positioned within the same lumen 215 as the cutting mechanism. This embodiment includes an opening 361 within the outer tubular member 1024, through which the tissue shield 250 may be advanced. In an embodiment, the tissue shield 250 is contained within an elongate tubular member 270 that extends within the lumen 215. The tubular member 270 may be either moveable or fixed with respect to the outer tubular member 1024. The tissue shield 250 is advanced within the tubular member 270, which retains it in a retracted configuration while the outer tubular member 1024 is delivered into a patient. The distal end 271 of tubular member 270 may be, for example, angled or curved towards the opening 361 so that the tissue shield 250 is directed through the opening 361 when it is extended towards its expanded configuration.

To use the system shown in FIGS. 1-8, the outer tubular member 1024 is introduced into a patient's body, preferably through a rigid shaft. The tissue shield 250 is then actuated by moving the expandable frame element 251 from its retracted configuration to an expanded configuration using a suitable actuation mechanism such as a pull wire in working arrangement with the housing 101. Such pull wires or similar triggering mechanisms are well known in the art. The expanded tissue shield 250 is placed into contact with tissue that is intended to be unaffected by the subsequent surgical procedure. Tissue intended to be resected is drawn into the window 1026, through the use of suction into the lumen 215 and/or by direct manipulation of the tissue. The tubular member 1024 may be repositioned as necessary to complete the surgical procedure and to resect all desired tissues. Once the procedure is complete, the expandable frame element 251 is moved to its retracted configuration, drawn into its delivery lumen and is thereafter removed from the patient.

The disclosed inventions provide tissue removal systems and related methods that may be used, without limitation, for removing tissue during laparoscopic surgery. The systems and methods make use of a tissue shield that serves to protect non-target tissues throughout the surgical procedure, thus enhancing safety and usability when compared with conventional devices. While aspects of the invention have been described with reference to example embodiments thereof, it will be understood by those skilled in the art that various changes in form and details may be made therein without departing from the scope of the invention as recited in the claims.

What is claimed is:

1. A tissue removal device, comprising:
   a cannula comprising a proximal end portion, a distal end portion, a sidewall, a lumen extending between the proximal end portion and the distal end portion, a first opening in the sidewall in the distal end portion and extending into the lumen, and a second opening in the sidewall in the distal end portion and extending into the lumen;
   a cutting blade movably disposed within the lumen and configured for cutting tissue that has prolapsed through the first opening; and
   a tissue shield movably disposed within the lumen and configured to be at least partially extended out the second opening and retracted back through the second opening into the lumen, the tissue shield comprising an expandable frame element extending from the second opening, the expandable frame element having a collapsed configuration and an expanded configuration, and a shield element attached to the expandable frame element, wherein the shield element is substantially taut when the expandable frame element is in the expanded configuration, wherein when the tissue removal device is inserted into body tissue with the first opening positioned adjacent targeted tissue to be removed, and the expandable frame is deployed out the second opening and in the expanded configuration, the shield element extends radially away from the second opening to hold non-targeted tissue away from the first opening, wherein the first opening is located at a position distal of the second opening, and the first and second openings are positioned approximately 180 degrees from each other in the sidewall.

2. The tissue removal device of claim 1, wherein the expandable frame element is inflatable to transition from the collapsed configuration to the expanded configuration.

3. The tissue removal device of claim 1, wherein the expandable frame self-expands from the collapsed configuration to the expanded configuration as the frame element is extended out the second opening.

4. A tissue removal device, comprising:
a first elongate tubular member comprising a first tubular member sidewall, a first tubular member lumen, and a tissue resection opening in a distal portion of the first tubular member sidewall, wherein the tissue resection opening is in communication with the first tubular member lumen;
a second elongate tubular member disposed adjacent to, and aligned with, the first tubular member, the second tubular member comprising a second tubular member sidewall, a second tubular member lumen, and a tissue shield opening in a distal portion of the second tubular member sidewall, wherein the tissue shield opening is in communication with the second tubular member lumen;
a tissue cutter movably disposed within the first tubular member lumen and configured for cutting tissue that has prolapsed through the tissue resection opening; and
a tissue shield movably disposed within the second tubular member lumen and configured to be at least partially deployed out the tissue shield opening and retracted back through the tissue shield opening into the second tubular member lumen, the tissue shield comprising
an expandable frame element having a collapsed configuration and an expanded configuration, and
a shield element attached to the frame, wherein the shield element is substantially taut when the frame element is in the expanded configuration, wherein when the tissue removal device is inserted into body tissue with the tissue resection opening positioned adjacent targeted tissue to be removed, and the expandable frame is deployed out the tissue shield opening and in the expanded configuration, the shield element extends radially away from the tissue shield opening to hold non-targeted tissue away from the tissue resection opening, wherein the tissue resection opening is located at a position distal of the tissue shield opening, and the tissue resection opening is facing a first direction and the tissue shield opening is facing a second direction opposite the first direction.

5. The tissue removal device of claim 4, wherein the expandable frame element is inflatable to transition from the collapsed configuration to the expanded configuration.

6. The tissue removal device of claim 5, further comprising an inflation tube attached to the expandable frame element and extending through the second tubular member lumen.

7. The tissue removal device of claim 4, wherein the shield element comprises an elastomeric polymer.

8. The tissue removal device of claim 4, wherein the shield element comprises a metallic mesh.

9. The tissue removal device of claim 4, wherein the second tubular member terminates at a position proximal to a distal end of the first tubular member.

10. The tissue removal device of claim 4, wherein the expandable frame element self-expands from the collapsed configuration to the expanded configuration as the frame element is extended out the tissue shield opening.

11. The tissue removal device of claim 10, wherein the expandable frame element comprises a shape memory material.

12. A method of removing tissue from a patient using a tissue removal device, the tissue removal device comprising a cutting cannula and tissue shield cannula, the cutting cannula comprising a lumen containing a movable cutting element, and defining a tissue resection window adjacent a closed distal end thereof, the tissue shield cannula comprising a lumen containing an expandable tissue shield and defining a tissue shield opening, wherein the tissue resection window is located at a position distal of the tissue shield opening, and the tissue resection window is facing a first direction and the tissue shield opening is facing a second direction opposite the first direction, the method comprising:
positioning the tissue removal device so that the tissue resection window is adjacent a targeted tissue in the patient;
deploying the tissue shield through the tissue shield opening so that an expandable frame portion of the tissue shield is extended out of the tissue shield cannula lumen and self-expands or is otherwise expanded so that a shield element attached to the expandable frame portion is substantially taut to thereby hold non-targeted tissue away from the tissue resection window; and
cutting the targeted tissue using the cutting element.

13. The method of claim 12, further comprising applying vacuum to the cutting cannula lumen so that the targeted tissue is drawn into the tissue resection window.

14. The method of claim 12, wherein positioning the tissue removal device comprises inserting the tissue removal device through a laparoscopic incision in the patient.

15. The method of claim 12, further comprising retracting the tissue shield back through the tissue shield opening into the tissue shield cannula lumen.

* * * * *